United States Patent
Dastoor et al.

(10) Patent No.: US 12,130,254 B2
(45) Date of Patent: Oct. 29, 2024

(54) ORGANIC THIN FILM TRANSISTORS AND THE USE THEREOF IN SENSING APPLICATIONS

(71) Applicant: LIFE SCIENCE BIOSENSOR DIAGNOSTICS PTY. LTD., Sydney Nsw (AU)

(72) Inventors: Paul Dastoor, Callaghan (AU); Warwick Belcher, Callaghan (AU)

(73) Assignee: LIFE SCIENCE BIOSENSOR DIAGNOSTICS PTY. LTD., Sydney (AU)

( * ) Notice: Subject to any disclaimer, the term of this patent is extended or adjusted under 35 U.S.C. 154(b) by 845 days.

(21) Appl. No.: 17/007,764

(22) Filed: Aug. 31, 2020

(65) Prior Publication Data

US 2020/0400608 A1 Dec. 24, 2020

Related U.S. Application Data

(63) Continuation of application No. 16/661,204, filed on Oct. 23, 2019, now abandoned, which is a
(Continued)

(30) Foreign Application Priority Data

Mar. 6, 2012 (AU) .................. 2012900885

(51) Int. Cl.
*H01L 51/00* (2006.01)
*B82Y 10/00* (2011.01)
(Continued)

(52) U.S. Cl.
CPC ......... *G01N 27/4145* (2013.01); *C12Q 1/006* (2013.01); *H10K 10/464* (2023.02); *H10K 10/471* (2023.02); *H10K 10/481* (2023.02)

(58) Field of Classification Search
CPC .. G01N 33/5438; G01N 27/126; H01L 29/78; H01L 51/0093
See application file for complete search history.

(56) References Cited

U.S. PATENT DOCUMENTS 5,215,887 A 6/1993 Saito
5,227,042 A 7/1993 Zawodzinski et al.
(Continued)

FOREIGN PATENT DOCUMENTS

JP JS57127841 A 8/1982
JP S61155850 A 7/1986
(Continued)

OTHER PUBLICATIONS

Liu, et al., "Glucose sensor based on organic thin film transistor using glucose oxidase and conducting polymer" Institute for Micromanufacturing, Louisiana Tech University, Ruston, LA 71272, USA, Sensors and Actuators B 135 (2008) 195-199.
(Continued)

*Primary Examiner* — Anthony Ho
*Assistant Examiner* — David J Goodwin
(74) *Attorney, Agent, or Firm* — Tarolli, Sundheim, Covell & Tummino LLP

(57) ABSTRACT

The present invention relates to organic thin film transistors and the preparation and use thereof in sensing applications, and in particular in glucose sensing applications.

18 Claims, 4 Drawing Sheets

Related U.S. Application Data continuation of application No. 15/679,765, filed on Aug. 17, 2017, now abandoned, which is a continuation of application No. 14/382,927, filed as application No. PCT/AU2013/000207 on Mar. 5, 2013, now Pat. No. 9,766,199.

(51) Int. Cl.
*C12Q 1/00* (2006.01)
*G01N 27/414* (2006.01)
*H10K 10/46* (2023.01)

(56) References Cited

U.S. PATENT DOCUMENTS

| | | | |
|---|---|---|---|
| 5,250,439 | A | 10/1993 | Musho et al. |
| 7,368,085 | B2* | 5/2008 | Gu .................... G01N 33/66 436/95 |
| 9,178,170 | B2* | 11/2015 | Yan .................... G01N 27/4145 |
| 9,709,560 | B2 | 7/2017 | Horesh |
| 9,910,007 | B2 | 3/2018 | Fuerst et al. |
| 2006/0272942 | A1* | 12/2006 | Sirringhaus ........ G01N 27/414 204/406 |
| 2010/0187107 | A1 | 7/2010 | Katsuki et al. |
| 2010/0224913 | A1 | 9/2010 | Chiang et al. |
| 2011/0068372 | A1* | 3/2011 | Ren .................... G01N 27/414 257/E29.246 |
| 2012/0244037 | A1* | 9/2012 | Matsumoto ........ G01N 27/4145 422/69 |
| 2014/0061728 | A1 | 3/2014 | Trivedi |
| 2014/0093902 | A1* | 4/2014 | Omenetto ................ B82Y 5/00 257/40 |
| 2014/0131774 | A1 | 5/2014 | Lee et al. |
| 2015/0037827 | A1 | 2/2015 | Dastoor et al. |
| 2016/0069834 | A1* | 3/2016 | Sakata ............... G01N 27/4166 204/403.01 |
| 2017/0157583 | A1 | 6/2017 | Kulkarni et al. |
| 2017/0343508 | A1 | 11/2017 | Dastoor et al. |
| 2018/0059051 | A1* | 3/2018 | Yang .................... G01N 33/552 |

FOREIGN PATENT DOCUMENTS

| | | |
|---|---|---|
| JP | S61274682 A | 12/1986 |
| JP | 2004105065 A | 4/2004 |
| JP | 200562569 A | 3/2005 |
| TW | 201338230 | 9/2013 |
| WO | 2018000012 A1 | 1/2018 |

OTHER PUBLICATIONS

El'skaya, A. et. al., "Glucose-sensitive field-effect transistor with additional Nafion membrane: Reduction of influence of buffer capacity on the sensor response and extension of its dynamic range", Analytica Chimica Acta, vol. 283, Issue 2, Nov. 26, 1993, pp. 695-701.
Nilsson, D. et al., "An all-organic sensor-transistor based on a novel electrochemical transducer concept printed electrochemical sensors on paper", Sensors and Actuators B: Chemical, vol. 86, Issues 2-3, Sep. 20, 2002, pp. 193-197.
Macaya, D et al., "Simple glucose sensors with micromolar sensitivity based on organic electrochemical transistors", Sensors and Actuators B: Chemical, vol. 123, Issue 1, Apr. 10, 2007, pp. 374-378.

Mabeck, J et al., "Chemical and biological sensors based on organic thin film transistors", Analytical and Bioanalytical Chemistry, Jan. 2006, vol. 384, Issue 2, pp. 343-353.
Zhou, Xiaojing, et al. "Effects of device architecture on the performance of organic thin film transistors." MRS Proceedings. Vol. 1138. Cambridge University Press, 2008.
Yao, Huanfen, et al. "A contact lens with embedded sensor for monitoring tear glucose level." Biosensors and Bioelectronics 26.7 (2011): 3290-3296.
Sirois, Kathleen, et al.: "Hygroscopic Insulator Organic Field-Effect Transistor for Biosensing Applications"; Abstract for presentation at Australian Institute of Physics 17th National Congress 2006; http://aipc2006.com/abstract/648.htm.
Roberts, Mark E., et al. "Water-stable organic transistors and their application in chemical and biological sensors." Proceedings of the National Academy of Sciences 105.34 (2008): 12134-12139.
Nikolou, Maria, and George G. Malliaras, "Applications of poly (3, 4-ethylenedioxythiophene) doped with poly (styrene sulfonic acid) transistors in chemical and biological sensors." The Chemical Record 8.1 (2008): 13-22.
Lin, Peng, and Feng Yan. "Organic Thin-Film Transistors for Chemical and Biological Sensing." Advanced materials 24.1 (2012): 34-51.
Fang, Alping, Hou Tee Ng, and Sam Fong Yau Li. "A high-performance glucose biosensor based on monomolecular layer of glucose oxidase covalently immobilised on indium-tin oxide surface." Biosensors and bioelectronics 19.1 (2003): 43-49.
Bartic, Carmen, and Gustaaf Borghs. "Organic thin-film transistors as transducers for (bio) analytical applications." Analytical and bioanalytical chemistry 384.2 (2006): 354-365.
Elkington, Daniel, et al. "Organic thin-film transistor (OTFT)-based sensors." Electronics 3.2 (2014): 234-254.
Elkington, D., et al. "Printable organic thin film transistors for glucose detection incorporating inkjet-printing of the enzyme recognition element." Applied Physics Letters 106.26 (2015): 64_1.
Elkington, D, et al. "Detection of saliva-range glucose concentrations using organic thin-film transistors," Applied Physics Letters (2014), vol. 105, pp. 043303-1-043303-4.
Fryczowska, B et al "Preparation and properties of composite PAN/PANI membranes," International Journal of Polymer Science (2017), vol. 2017.
Bae, J et al., "Field-Effect Transistors Based on Organic and Carbon-Based Materials for Chemical and Biological Sensors," Current Organic Chemistry (2015), vol. 19, No. 12, pp. 1176-1190.
Torsi, L., et al., "Organic thin-film transistors as plastic analytical sensors," Analytical Chemistry (2005), pp. 380-A to 387-A.
Liao, C et al, "Organic Semiconductors in Organic Thin-Film Transistor-Based Chemical and Biological Sensors" Polymer Reviews 53:3 352-406, 2013.
Darwis et al, "Novel low voltage and solution processable organic thin film transistors based on water dispersed polymer semiconductor nanoparticulates" Journal of Colloid and Interface Science, 401, 65-69, 2013.
Yan, H et al, "A high-mobility electron-transporting polymer for printed transistors" Nature 475, 5, 2009.
Holmes, Natalie et al, "The effect of polymer molecular weight on P3HT:PCBM nanoparticulate organic photovoltaic device performance" Solar Energy Materials & Solar Cells 128 369-377 2014.
Jiang et al. "Static and Dynamic modelling of organic thin-film transistors for circuit design" Microelectronics Journal, 53 (2016) 1-7, cited in the Korean office action for the related patent family (U.S. Appl. No. 17/226,685).
Huaiguo Xue et al., 'A highly stable biosensor for phenols prepared by immobilizing polyphenol oxidase into polyaniline-polyacrylonitrile composite matrix', Talanta, vol. 57 issue 2, p. 289-295.

* cited by examiner

ORGANIC THIN FILM TRANSISTORS AND THE USE THEREOF IN SENSING APPLICATIONS

The present invention is a continuation of U.S. patent application Ser. No. 16/661,204, filed on 23 Oct. 2019, which is a continuation of U.S. patent application Ser. No. 15/679,795, filed on 17 Aug. 2017, which is a continuation of U.S. patent application Ser. No. 14/382,927, filed on 4 Sep. 2014, which is a U.S. National Stage under 35 USC 371 patent application, claiming priority to Serial No. PCT/AU2013/000207, filed on 5 Mar. 2013; which claims priority from AU 2012900885, filed 6 Mar. 2012, the entirety of which is incorporated herein by reference.

TECHNICAL FIELD

The present invention relates to organic thin film transistors and the preparation and use thereof in sensing applications, and in particular in glucose sensing applications.

BACKGROUND OF THE INVENTION

The development of organic thin film transistors (OTFTs) has grown rapidly in recent years motivated primarily by the unique physical properties of polymer devices, including their flexibility and ability to be fabricated using low-cost, solution-based techniques. Work on developing OTFTs for new and existing applications has focussed on two main areas. First, there have been systematic improvements in the materials and fabrication processes which have lead to an improvement in the conventional performance parameters of organic devices making them comparable to their inorganic counterparts. Second, improvements in film morphology of the organic semiconductor layer have been made with the goal of eliminating electron and/or hole traps and enhancing free carrier transport in the polymer semiconducting materials. Progress has also been made in developing high capacitance organic dielectric layers and large improvements in OTFT performance have been reported. The inherent compatibility of organic materials with biological molecules makes OTFTs suitable for use in biosensing applications.

The present inventors have successfully fabricated an OTFT device that is capable of sensing glucose levels across a broad range of concentrations and which is straightforward and cheap to manufacture. The device opens the way for a commercially viable glucose sensor that allows blood glucose concentration to be estimated by detecting the level of glucose in saliva as opposed to blood. Such a device would obviate the need for diabetic patients to obtain a blood sample when determining their blood glucose level.

SUMMARY OF THE INVENTION

In a first aspect, the present invention provides a transistor device comprising:
 (i) a gate electrode;
 (ii) a dielectric layer,
 (iii) a semiconducting layer comprising at least one organic compound,
 (iv) a source electrode,
 (v) a drain electrode,
 (vi) a substrate, and
 (vii) an enzyme.

The gate electrode may be disposed above the dielectric layer.

The dielectric layer may be disposed above the semiconducting layer.

The semiconducting layer may be disposed above and in between the source electrode and the drain electrode.

The source electrode and the drain electrode may be disposed above the substrate.

The gate electrode may be disposed above, and in direct contact with, the dielectric layer.

The dielectric layer may be disposed above, and in direct contact with, the semiconducting layer.

The semiconducting layer may be disposed above and in between the source electrode and the drain electrode, and in direct contact with, the source electrode and the drain electrode.

The source electrode and the drain electrode may be disposed above, and in direct contact with, the substrate.

The gate electrode may comprise, consist of, or consist essentially of, a porous matrix.

The porous matrix may be a sulfonated tetrafluoroethylene-based fluoropolymer-copolymer.

The sulfonated tetrafluoroethylene-based fluoropolymer-copolymer may be ethanesulfonic acid, 2-[1-[difluoro[(1,2,2-trifluoroethenyl)oxy]methyl]-1,2,2,2-tetrafluoroethoxy]-1,1,2,2-tetrafluoro-, polymer with 1,1,2,2-tetrafluoroethene.

The dielectric layer may comprise, consist of, or consist essentially of, poly(4-vinylphenol).

The enzyme may be located in, or form part of, the gate electrode.

The enzyme may be located in, or form part of, the dielectric layer.

The at least one organic compound may be poly(3-hexylthiophene).

The source and/or drain electrodes may comprise, consist, or consist essentially of indium tin oxide (ITO), for example pre-patterned ITO.

The semiconducting layer may have a thickness between about 5 nm and about 500 nm, or between about 75 nm and about 125 nm, or about 100 nm.

The dielectric layer may have a thickness between about 50 nm and 750 nm, or between about 300 nm and about 500 nm, or about 400 nm.

The gate electrode may be offset with respect to the dielectric layer.

The enzyme may be glucose oxidase.

The device of the first aspect may be a device for sensing glucose in a sample/analyte, for example in a bodily fluid such as saliva.

In a second aspect, the present invention provides a method for preparing a transistor device as defined in the first aspect comprising:
 a) depositing the source electrode and the drain electrode over the substrate;
 b) depositing the semiconducting layer comprising at least one organic compound over the source electrode and the drain electrode;
 c) depositing the dielectric layer over the semiconducting layer;
 d) depositing the gate electrode over the dielectric layer, wherein the enzyme is introduced into the device as part of any one or more of steps a) to d).

The enzyme may be introduced into the device as part of step d) and/or as part of step c).

Step a) may comprise depositing the source electrode and the drain electrode over the substrate such that the source electrode and the drain electrode are disposed above, and in direct contact with, the substrate.

Step b) may comprise depositing the semiconducting layer comprising at least one organic compound over the source electrode and the drain electrode such that the semiconducting layer is disposed above and in between the source electrode and the drain electrode.

Step b) may comprise depositing the semiconducting layer comprising at least one organic compound over the source electrode and the drain electrode such that the semiconducting layer is disposed above and in between the source electrode and the drain electrode, and in direct contact with, the source electrode and the drain electrode.

Step c) may comprise depositing the dielectric layer over the semiconducting layer, such that the dielectric layer is disposed above, and in direct contact with, the semiconducting layer.

Step c) may comprise forming a mixture of a dielectric material and the enzyme and depositing the mixture over the semiconducting layer to form the dielectric layer.

Step c) may comprise forming a mixture of a dielectric material and the enzyme and depositing the mixture over the semiconducting layer to form the dielectric layer, such that the dielectric layer is disposed above, and in direct contact with, the semiconducting layer.

Step d) may comprise depositing the gate electrode over the dielectric layer, such that the gate electrode is disposed above, and in direct contact with, the dielectric layer.

Step d) may comprise forming a mixture of a porous matrix and an enzyme and depositing the mixture over the dielectric layer to form the gate electrode.

Step d) may comprise forming a mixture of a porous matrix and an enzyme and depositing the mixture over the dielectric layer to form the gate electrode, such that the gate electrode is disposed above, and in direct contact with, the dielectric layer.

The semiconducting layer and/or the dielectric layer may be deposited by spin coating.

The semiconducting layer may be deposited so as to achieve a thickness between about 5 nm and about 500 nm, or between about 75 nm and about 125 nm, or about 100 nm.

The dielectric layer and the at least one organic compound may be as defined in the first aspect, and hereinafter.

The dielectric layer may be applied so as to achieve a thickness between about 50 nm and 750 nm, or between about 300 nm and about 500 nm, or about 400 nm.

The source and drain electrodes may be as defined in the first aspect, and hereinafter.

In a third aspect, the present invention provides use of the device of the first aspect for sensing a compound in a sample/analyte.

The compound may be glucose.

The sample/analyte may be a bodily fluid, for example saliva.

In a fourth aspect, the present invention provides a method for determining a concentration or an amount of a compound in a sample/analyte comprising the compound, the method comprising the following steps:
  a) providing a device of the first aspect;
  b) applying a gate voltage and a drain voltage to the device;
  c) contacting the sample/analyte with the device;
  d) detecting drain current; and
  e) determining the concentration or the amount of the compound based on the magnitude of the drain current.

The compound may be glucose.

Step c) may comprise contacting the sample/analyte with the gate electrode.

The gate voltage and drain voltage applied may be voltages greater than that required to liberate $H^+$ from $H_2O_2$, and lower than that required to cause electrolysis of water.

The gate voltage and drain voltage applied may be between about 0 V and −2 V, or about −1 V.

The sample/analyte may be a bodily fluid, for example saliva.

In a fifth aspect the present invention provides a device whenever prepared by the method of the second aspect.

BRIEF DESCRIPTION OF THE FIGURES

A preferred embodiment of the present invention will now be described, by way of example only, with reference to the accompanying drawings wherein.

DEFINITIONS

Figure 1:
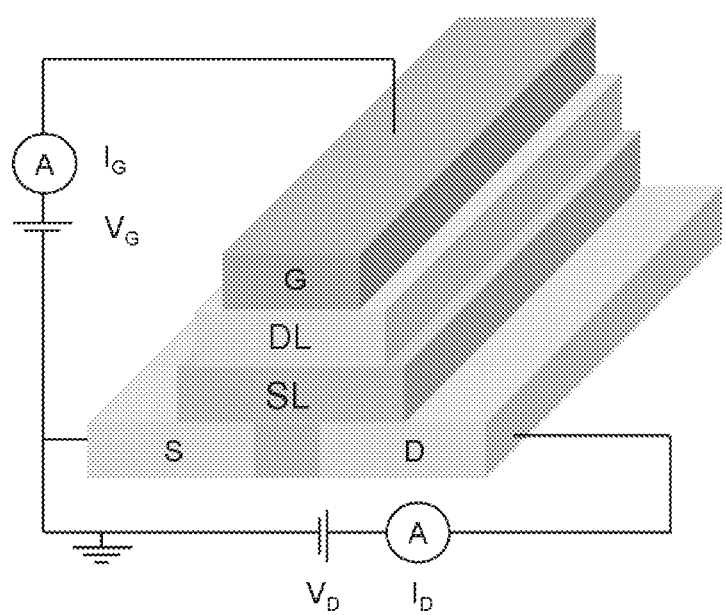
FIG. 1 shows the structure of a HIOT device in accordance with one embodiment of the invention.

The following are some definitions that may be helpful in understanding the description of the present invention. These are intended as general definitions only and should in no way limit the scope of the present invention to those terms alone, but are put forth for a better understanding of the following description.

Throughout this specification, unless the context requires otherwise, the word "comprise", or variations such as "comprises" or "comprising", will be understood to imply the inclusion of a stated step or element or integer or group of steps or elements or integers, but not the exclusion of any other step or element or integer or group of elements or integers. Thus, in the context of this specification, the term "comprising" means "including principally, but not necessarily solely".

In the context of this specification, the term "about" is understood to refer to a range of numbers that a person of skill in the art would consider equivalent to the recited value in the context of achieving the same function or result.

In the context of this specification, the terms "a" and "an" refer to one or to more than one (i.e. to at least one) of the grammatical object of the article. By way of example, "an element" means one element or more than one element.

In the context of this specification, the term "bodily fluid" is understood to include any liquid which originates within a human or animal body, including fluids that are secreted or excreted. Non-limiting examples of bodily fluids include: blood, saliva, sweat, urine, breast milk, bile and peritoneal fluid.

In the context of this specification, the term "top" means farthest away from the substrate, and the term "bottom" means closest to the substrate. Where a first layer is described as "disposed above" a second layer, the first layer is disposed farther away from the substrate. Furthermore, where a first layer is described as being "disposed above" a second layer, additional intermediate layers may be present in between the first and second layers, unless it is specified that the first layer is "in direct contact with" the second layer.

DETAILED DESCRIPTION OF THE INVENTION

In one aspect, the present invention provides a transistor device comprising:
(i) a gate electrode;
(ii) a dielectric layer,
(iii) a semiconducting layer comprising at least one organic compound,
(iv) a source electrode,
(v) a drain electrode,
(vi) a substrate, and
(vii) an enzyme.

In the devices of the present invention the gate potential controls the doping and de-doping of the semiconducting compound(s) via ion migration from the dielectric layer into the active channel. Accordingly, in order to accurately reflect their electronic behaviour, the present devices are referred to herein as "hygroscopic insulator organic transistors" (HIOTs).

In one embodiment, the gate electrode may be disposed above the dielectric layer. In another embodiment the dielectric layer may be disposed above the semiconducting layer. In a further embodiment the semiconducting layer may be disposed above and in between the source electrode and the drain electrode. In yet another embodiment, the source electrode and the drain electrode may be disposed above the substrate.

In another embodiment, the gate electrode may be disposed above, and in direct contact with, the dielectric layer. In still a further embodiment the dielectric layer may be disposed above, and in direct contact with, the semiconducting layer. In yet another embodiment the semiconducting layer may be disposed above and in between the source electrode and the drain electrode, and in direct contact with, the source electrode and the drain electrode. In still a further embodiment, the source electrode and the drain electrode may be disposed above, and in direct contact with, the substrate.

The gate electrode may comprise, consists of, or consist essentially of, a porous matrix. The porous matrix may be a sol-gel material. In one embodiment the porous matrix is a sulfonated tetrafluoroethylene-based fluoropolymer-copolymer, for example a copolymer comprising a tetrafluoroethylene backbone and perfluoroalkyl ether groups terminated with sulfonate groups. The sulfonated tetrafluoroethylene-based fluoropolymer-copolymer may be a copolymer of tetrafluoroethylene and perfluoro-3,6-dioxa-4-methyl-7-octene-sulfonic acid that is commercially available from E. I. du Pont de Nemours and Company, Wilmington DE, USA, under the tradename Nafion®. In an alternative embodiment, the sulfonated tetrafluoroethylene-based fluoropolymer-copolymer is ethanesulfonic acid, 2-[1-[difluoro[(1,2,2-trifluoroethenyl)oxy]methyl]-1,2,2,2-tetrafluoroethoxy]-1,1,2,2-tetrafluoro-, polymer with 1,1,2,2-tetrafluoroethene, which is commercially available from Sigma-Aldrich, Castle Hill, NSW, Australia.

The dielectric layer may comprise, consist of, or consist essentially of a dielectric material, such as for example polyvinyl phenols, including poly(4-vinylphenol). Alternative dielectric materials that may be used in the devices will be readily apparent to those skilled in the art. Non-limiting examples include polyimide and poly(methyl methacrylate) (PMMA). In alternative embodiments the dielectric layer may comprise a doped dielectric material, for example lithium perchlorate doped poly(4-vinylpyridine).

The dielectric layer may have a thickness between about 50 nm and 750 nm, or between about 100 nm and about 700 nm, or between about 100 nm and about 600 nm, or between about 200 nm and about 500 nm, or between about 300 nm and about 500 nm, or between about 350 nm and about 450 nm, or about 400 nm.

Organic compounds suitable for use in the semiconducting layer include any organic compound having semiconducting properties. Examples of suitable organic compounds include, but are not limited to: polyacetylenes, porphyrins, phthalocyanins, fullerenes, polyparaphenylenes, polyphenylenevinylenes, polyfluorenes, polythiophenes, polypyrroles, polypyridines, polycarbazoles, polypyridinevinylenes, polyarylvinylenes, poly (p-phenylmethylvinylenes), including derivatives and co-polymers thereof, and further including mixtures thereof.

In one embodiment of the invention the at least one organic compound is selected from the group consisting of: poly(9,9-dioctylfluorene-2,7-diyl-co-bis-N,N-(4-butylphenyl)-bis-N,N-phenyl-1,4-phenylenediamine), poly(9,9-dioctylfluorene-2,7-diyl-co-benzothiadiazole), poly(3-hexylthiophene), (6,6)-phenyl-$C_{61}$-butyric acid methyl ester and poly(2-methoxy-5-(2'-ethyl-hexyloxy)-1,4-phenylene vinylene). Also contemplated are mixtures of one or more of the above noted organic compounds.

The semiconducting layer may have a thickness between about 5 nm and about 500 nm, or between about 5 nm and about 300 nm, or between about 50 nm and about 250 nm, or between about 75 nm and about 125 nm, or about 100 nm.

The source and drain electrodes may comprise, consist of, or consist essentially of ITO or pre-patterned ITO, however those skilled in the art will recognise that the source and drain electrodes may comprise, consist, or consist essentially of alternative materials, such as, for example, graphene and other metals, including gold and silver.

The substrate may be glass, or any other suitable substrate known to those skilled in the art, for example paper or low-cost plastics, such as polyethylene terephthalate (PET).

The device may have a channel length of between about 5 μm and about 50 μm, or between about 10 μm and about 30 μm, or about 20 μm, and a channel width of between about 1 mm and about 20 mm, or between about 1 mm and about 10 mm, or about 3 mm.

The device further comprises an enzyme. The enzyme may be located in, or form part of, any of the components of the device, i.e., the enzyme may be located in, or form part of, the gate electrode, the dielectric layer, the semiconducting layer, the source electrode, or the drain electrode. The enzyme may also be located in, or form part of, the channel. In certain embodiments of the invention the enzyme is located in, or forms part of, the dielectric layer, or the enzyme is located in, or forms part of, the gate electrode. The gate electrode may comprise, consist of, or consist essentially of the porous matrix and the enzyme. The enzyme (for example glucose oxidase) may be uniformly distributed throughout the porous matrix.

FIG. 1 shows the structure of a HIOT device in accordance with one embodiment of the invention. This device is a top gate bottom contact thin film transistor comprising a gate electrode G, located at the top of the device, the gate electrode being disposed above, and in direct contact with, the dielectric layer DL, the dielectric layer DL being disposed above, and in direct contact with, the semiconducting layer SL, the semiconducting layer SL being disposed above and in between the source electrode S and the drain electrode D, and in direct contact with, the source electrode S and the drain electrode D, the source electrode S and the drain electrode D being disposed above, and in direct contact with, the substrate (not shown). The substrate is located at the bottom of the device.

In an embodiment of the first aspect the invention provides a transistor device comprising: a gate electrode comprising a porous matrix and an enzyme, the gate electrode being disposed above, and in direct contact with, a dielectric layer, the dielectric layer being disposed above, and in direct contact with, a semiconducting layer, the semiconducting layer being disposed above and in between a source electrode and a drain electrode, and in direct contact with, the source electrode and the drain electrode, the source electrode and the drain electrode being disposed above, and in direct contact with, a substrate.

In another embodiment of the first aspect the invention provides a transistor device comprising: a gate electrode comprising a sulfonated tetrafluoroethylene-based fluoropolymer-copolymer and glucose oxidase, the gate electrode being disposed above, and in direct contact with, a dielectric layer, the dielectric layer being disposed above, and in direct contact with, a semiconducting layer, the semiconducting layer being disposed above and in between a source electrode and a drain electrode, and in direct contact with, the source electrode and the drain electrode, the source electrode and the drain electrode being disposed above, and in direct contact with, a substrate.

In the above embodiments the devices may be termed top gate bottom contact thin film transistors.

The devices of the invention may be used for sensing glucose in a sample/analyte, for example a bodily fluid or alternatively non-bodily fluids. Accordingly, the devices may be referred to as transistor-based sensor devices. In embodiments of the invention the bodily fluid is saliva, although those skilled in the art will recognise that the device may be used to sense glucose in other bodily fluids. The devices of the invention may also be used for sensing other compounds.

Devices in accordance with the present invention may be fabricated by low-cost spin-coating and printing techniques, thereby offering the potential for affordable and disposable non-reversible devices for sensing glucose. All of the components of the device are capable of being printed.

In another aspect, the present invention provides a method for preparing a transistor device as defined in the first aspect comprising:
  a) depositing the source electrode and the drain electrode over the substrate;
  b) depositing the semiconducting layer comprising at least one organic compound over the source electrode and the drain electrode;
  c) depositing the dielectric layer over the semiconducting layer;
  d) depositing the gate electrode over the dielectric layer, wherein the enzyme is introduced into the device as part of any one or more of steps a) to d).

In one embodiment, step a) may comprise depositing the source electrode and the drain electrode over the substrate such that the source electrode and the drain electrode are disposed above, and in direct contact with, the substrate. In another embodiment, step b) may comprise depositing the semiconducting layer comprising at least one organic compound over the source electrode and the drain electrode such that the semiconducting layer is disposed above and in between the source electrode and the drain electrode, and in direct contact with, the source electrode and the drain electrode. In another embodiment step c) may comprise depositing the dielectric layer over the semiconducting layer, such that the dielectric layer is disposed above, and in direct contact with, the semiconducting layer. In a further embodiment, step d) may comprise depositing the gate electrode over the dielectric layer, such that the gate electrode is disposed above, and in direct contact with, the dielectric layer.

The semiconducting layer and/or the dielectric layer may be deposited in accordance with methods well known to those skilled in the art, including, but not limited to: electroplating, vapour phase deposition, spin coating, screen printing, ink-jet printing, slot-dye printing, spray coating, draw bar coating or derived coating/printing techniques thereof, painting, gravure, roller and embossing. In one embodiment, the semiconducting layer and/or the dielectric layer are deposited by spin coating.

In some embodiments, the semiconducting layer may be deposited so as to achieve a thickness between about 5 nm and about 500 nm, or between about 5 nm and about 300 nm, or between about 50 nm and about 250 nm, or between about 75 nm and about 125 nm, or about 100 nm.

In some embodiments, the dielectric layer may be applied so as to achieve a thickness between about 50 nm and 750 nm, or between about 100 nm and about 700 nm, or between about 100 nm and about 600 nm, or between about 200 nm and about 500 nm, or between about 300 nm and about 500 nm, or between about 350 nm and about 450 nm, or about 400 nm.

In embodiments of the invention the enzyme is introduced into the device as part of step c). Step c) may therefore comprise forming a mixture of a dielectric material and the enzyme and depositing the mixture over the semiconducting layer to form the dielectric layer. Alternatively, step c) may comprise forming a mixture of a dielectric material and the enzyme and depositing the mixture over the semiconducting layer to form the dielectric layer, such that the dielectric layer is disposed above, and in direct contact with, the semiconducting layer.

In other embodiments of the invention the enzyme is introduced into the device as part of step d). Step d) may therefore comprise forming a mixture of the porous matrix and the enzyme and depositing the mixture over the dielectric layer to form the gate electrode. Alternatively, step d) may comprise forming a mixture of the porous matrix and the enzyme and depositing the mixture over the dielectric layer to form the gate electrode, such that the gate electrode is disposed above, and in direct contact with, the dielectric layer.

The gate electrode may be deposited by methods known to those skilled in the art, for example drop casting, vapour deposition, sputtering and printing, including ink-jet, gravure, flexographic and doctor blade. In one embodiment, the gate electrode is deposited by drop casting a mixture of the porous matrix and the enzyme.

In a further aspect, the present invention provides a method for determining a concentration or an amount of a compound in a sample/analyte comprising the compound, the method comprising the following steps:
  (a) providing a device of the first aspect;
  (b) applying a gate voltage and a drain voltage to the device;
  (c) contacting the sample/analyte with the device;
  (d) detecting drain current; and
  (e) determining the concentration or the amount of the compound based on the magnitude of the drain current.

The compound may be glucose. Step c) may comprise contacting the sample/analyte with the gate electrode. Alternatively, the sample/analyte may be contacted with any other part of the device. In one embodiment, the sample/analyte is contacted with a component of the device which comprises the enzyme.

In one embodiment of this aspect, a gate voltage and a drain voltage are applied to the device of the first aspect and a sample/analyte comprising glucose, for example a bodily fluid such as saliva, is contacted with the gate electrode which comprises glucose oxidase (GOX). Glucose in the sample is degraded via an enzymatic reaction with GOX thereby producing $H_2O_2$. The gate voltage and drain voltage applied cause electrolysis of $H_2O_2$ thereby liberating $H^+$ ions. The increase in $H^+$ ions results in an increase in drain current, such that a relationship is established between the amount of glucose present in the sample/analyte and the magnitude of the drain current.

The gate voltage and drain voltage applied may be voltages greater than that required to liberate $H^+$ from $H_2O_2$, and lower than that required to cause electrolysis of water, as electrolysis of water may lead to a decrease in the signal-to-noise ratio of the sensor. Preferably, the gate voltage and drain voltage applied are between about 0 V and −2 V, or preferably about −1 V.

Step e) may be performed by reference to an appropriate calibration curve.

EXAMPLES

The invention will now be described in more detail, by way of illustration only, with respect to the following examples. The examples are intended to serve to illustrate this invention and should in no way be construed as limiting the generality of the disclosure of the description throughout this specification.

Device Fabrication and Characterisation
Fabrication and Characterisation of a Device Comprising a PEDOT:PSS Gate Despite previous studies, there remain several aspects of the operation of HIOT devices that are not well-understood and which need to be addressed if they are to be optimised for use in sensing applications. In particular, the origin of the transistor-like behaviour and the roles of the dielectric and gate materials in determining device operation are still not fully understood.

In order to understand the origin of the transistor-like behaviour and the roles of the dielectric and gate materials, a top gate, bottom contact thin film transistor was fabricated as follows: Pre-patterned ITO on glass slides (Kintec) was used for the source and drain electrodes, with a channel length of 20 μm and a width of 3 mm. A layer of poly (3-hexyl-thiophene) (P3HT) (Lumtec) with 100 nm thickness was spin-coated on top of the ITO as the semiconducting layer. Poly (4-vinylphenol) (Aldrich) was spin-coated on top of the P3HT layer with a thickness of approximately 400 nm. Poly (3,4-ethylenedioxythiophene):poly(styrene sulfonate) (PEDOT:PSS) (Stark) was drop-cast from an aqueous solution to form the gate electrode.

Figure 2A:
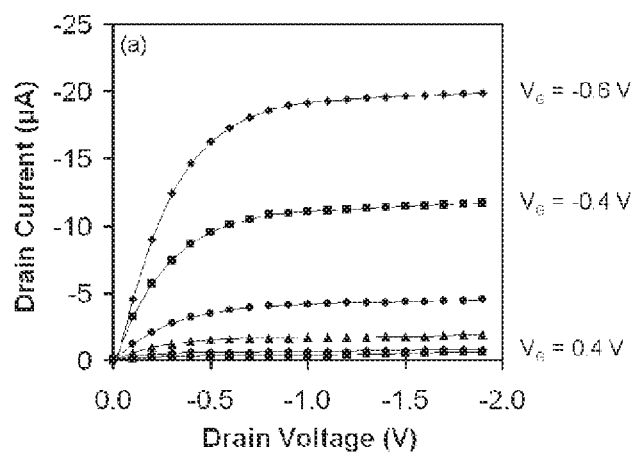
FIG. 2A shows a plot of drain voltage versus drain current in a HIOT device with a PEDOT:PSS gate measured in air.
Figure 2B:
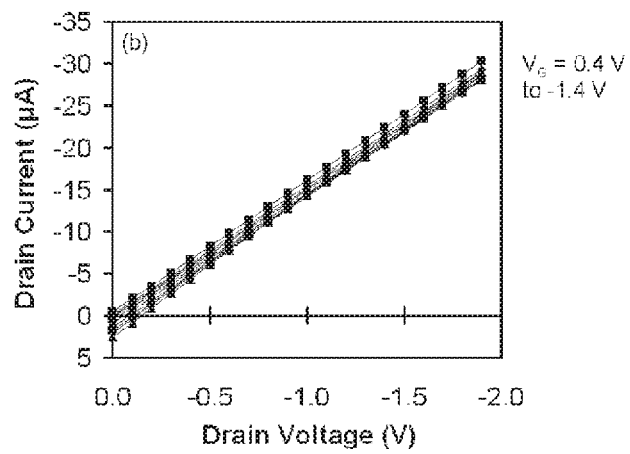
FIG. 2B shows a plot of drain voltage versus drain current in a HIOT device with a PEDOT:PSS gate measured in a dry environment.

When characterising the devices, the gate voltage ($V_G$) and drain voltage ($V_D$) are controlled, whilst the drain current ($I_D$) is monitored. These HIOT devices exhibited transistor-like output characteristics (with clearly defined linear and saturation regions), low operating voltages and current modulation ratios of between 10 and 100 (see FIG. 2 (a)). When measured in a dry atmosphere ($N_2$-filled glove box), there is no current modulation (FIG. 2 (b)), confirming the postulation that ionic movement is responsible for the transistor characteristics, and that these ions are not available once moisture is removed from the environment. However, the current levels of the device when measured in the glove box are relatively high—approximately equivalent to the on current of the device when measured in air. Therefore, without wishing to be bound by theory, it would appear that ionic movement in the device actually contributes to de-doping of the device. Again without wishing to be bound by theory, it is suggested that groups of ions, both positive and negative, are free to move within the dielectric layer and that their position changes depending on the voltages at the three electrodes, thereby influencing $I_D$.

Fabrication and Characterisation of a Device Comprising a Nafion:GOX Gate

A top gate, bottom contact thin film transistor in accordance with one embodiment of the present invention was fabricated as follows: Pre-patterned ITO on glass slides (Kintec) was used for the source and drain electrodes, with a channel length of 20 μm and a width of 3 mm. A layer of poly (3-hexyl-thiophene) (P3HT) (Lumtec) with 100 nm thickness was spin-coated on top of the ITO as the semiconducting layer. Poly (4-vinylphenol) (Aldrich) was spin-coated on top of the P3HT layer with a thickness of approximately 400 nm. A Nafion:GOX mixture comprising 20 mg/mL of GOX added to the as-received Nafion solution (Product Number 274704—Sigma-Aldrich Pty. Ltd., Castle Hill NSW, Australia) was drop cast to form the gate electrode. The device architecture is depicted in FIG. 1. In other embodiments, a mixture comprising between 2 mg/mL and 20 mg/mL of GOX may be used.

Figure 3:
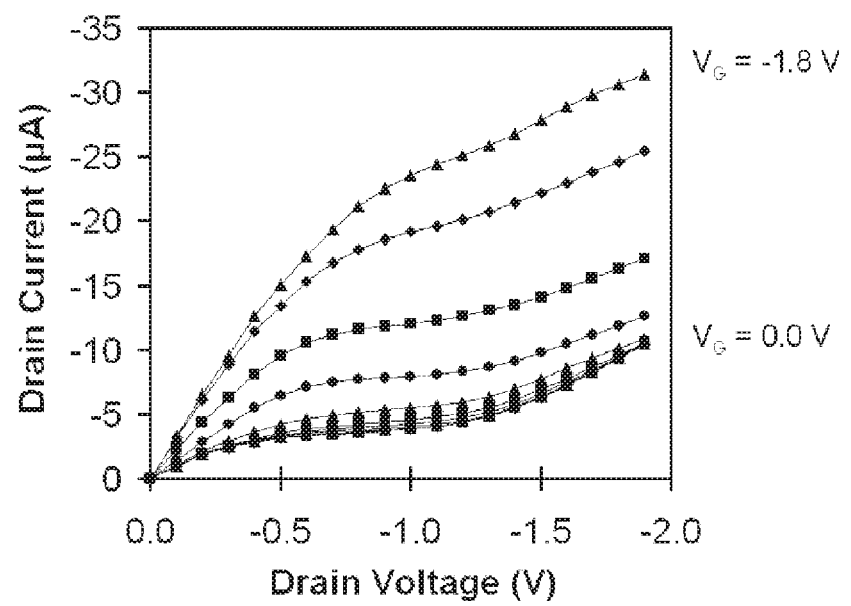
FIG. 3 shows the output characteristics of a Nafion:GOX gate HIOT device in accordance with one embodiment of the invention.

FIG. 3 shows the output characteristic of the Nafion:GOX gate device. Despite the slightly higher operating voltage required and the lower current modulation ratio (owing to a higher off current), the device shows the desired transistor-like characteristic which confirms it's suitability for use in a glucose sensor.

GOX breaks down glucose into $H_2O_2$ amongst other by-products, and the electrolysis of $H_2O_2$ occurs at a voltage of 0.7 V, which liberates $H^+$ ions. Accordingly, in order to bias the device appropriately, the voltage required to liberate ions from the $H_2O_2$ should be available, however the voltage should preferably not exceed the potential difference required to cause electrolysis of water (1.23 V) which would decrease the signal-to-noise ratio of the sensor.

Figure 4:
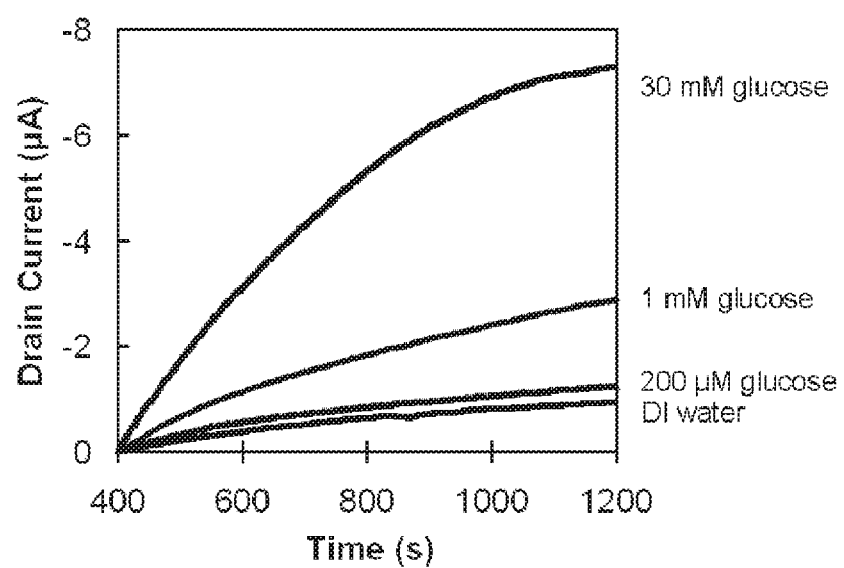
FIG. 4 shows the change in current obtained for a Nafion:GOX gate HIOT device in accordance with one embodiment of the invention for different concentrations of glucose in water.

For the sensing measurements, the device was biased at $V_D=V_G=-1$ V and 10 μL of analyte solution (various glucose concentrations in water) was dropped on top of the device (i.e. onto the gate which comprises the GOX) whilst $I_D$ was measured as a function of time. FIG. 4 shows the change in $I_D$ as a function of time for four different concentrations of glucose. The data is normalised by subtraction at 100 s after the analyte is dropped on the device. Clearly, there is a relationship between glucose concentration and the change in current. Glucose sensing with GOX incorporated into the Nafion gate was successfully demonstrated. The $H_2O_2$ librated by the enzymatic reaction on glucose and its subsequent electrolysis leads to additional ions in the system which has a similar effect to increasing the level of $V_G$ to achieve a higher $I_D$.

The claims defining the invention are as follows:
1. Use of an organic thin film transistor based biosensor device for sensing a compound in a sample/analyte, the device including:
(i) a gate electrode, wherein the gate electrode comprises a porous matrix comprising a sulfonated tetrafluoroethylene-based fluoropolymer-copolymer;

(ii) a dielectric layer;
(iii) a semiconducting layer including at least one organic compound;
(iv) a source electrode;
(v) a drain electrode;
(vi) a substrate; and
(vii) an enzyme located in, or forming part of any one of (i)-(vi).

2. The use of claim 1, wherein the semiconducting layer is disposed above and in between the source electrode and the drain electrode.

3. The use of claim 1, wherein the source electrode and the drain electrode are disposed above the substrate.

4. The use of claim 1, wherein the sulfonated tetrafluoroethylene-based fluoropolymer-copolymer is a copolymer comprising a tetrafluoroethylene backbone and perfluoroalkyl ether groups terminated with sulfonate groups.

5. The use of claim 4, wherein the sulfonated tetrafluoroethylene-based fluoropolymer-copolymer is ethanesulfonic acid, 2-[1-[difluoro[(1,2,2-trifluoroethenyl)oxy]methyl]-1,2,2,2-tetrafluoroethoxy]-1,1,2,2-tetrafluoro-, polymer with 1,1,2,2-tetrafluoroethene.

6. The use of claim 1, wherein the dielectric layer comprises poly(4-vinylphenol) or lithium perchlorate-doped poly(4-vinylpyridine).

7. The use of claim 1, wherein the enzyme is located in, or forms part of, the gate electrode.

8. The use of claim 1, wherein the enzyme is located in, or forms part of, the dielectric layer.

9. The use of claim 1, wherein the at least one organic compound is poly(3-hexylthiophene).

10. The use of claim 1, wherein the semiconducting layer has a thickness between about 5 nm and about 500 nm.

11. The use of claim 1, wherein the dielectric layer has a thickness between about 50 nm and 750 nm.

12. The use according to claim 1, wherein the enzyme is glucose oxidase.

13. The use according to claim 1, wherein the gate electrode comprises a sulfonated tetrafluoroethylene-based fluoropolymer-copolymer and glucose oxidase, the gate electrode being disposed above, and in direct contact with, the dielectric layer, the dielectric layer being disposed above, and in direct contact with, the semiconducting layer, the semiconducting layer being disposed above and in between the source electrode and the drain electrode, and in direct contact with, the source electrode and the drain electrode, the source electrode and the drain electrode being disposed above, and in direct contact with, the substrate.

14. The use of claim 1, wherein the sample or analyte is a bodily fluid.

15. The use of claim 1, wherein the sample or analyte is saliva.

16. The use of claim 1, wherein the compound is glucose.

17. The use of claim 1, wherein the device has top gate bottom contact configuration such that the gate electrode is disposed above the dielectric layer, and the dielectric layer is disposed above the semiconducting layer.

18. A method for determining a concentration or an amount of a compound in a sample/analyte comprising the compound, the method comprising:
a) providing an organic thin film transistor based biosensor device including:
(i) a gate electrode, wherein the gate electrode comprises a porous matrix comprising a sulfonated tetrafluoroethylene-based fluoropolymer-copolymer;
(ii) a dielectric layer;
(iii) a semiconducting layer including at least one organic compound;
(iv) a source electrode;
(v) a drain electrode;
(vi) a substrate; and
(vii) an enzyme located in, or forming part of any one of (i)-(vi),
b) applying a gate voltage and a drain voltage to the device;
c) contacting the sample/analyte with the device;
d) detecting drain current; and
e) determining the concentration or the amount of the compound based on the magnitude of the drain current.

* * * * *